in each case based on the total microemulsion, where the total of the amounts of components A, B, C, D, E and F is 100% by weight and where the microemulsion does not comprise any anionic surfactants, and to a process for the preparation of this microemulsion and to the use of this microemulsion for the treatment of plants.

US009901093B2

(12) United States Patent
Taranta et al.

(10) Patent No.: US 9,901,093 B2
(45) Date of Patent: Feb. 27, 2018

(54) MICROEMULSION HAVING WIDE APPLICATION RANGE

(75) Inventors: Claude Taranta, Stutensee (DE); Wolfgang Meier, Limburgerhof (DE); Thomas Bork, Westhofen (DE); Karl Strauss, Limburgerhof (DE); Tatjana Levy, Mannheim (DE); Jurith Montag, Limburgerhof (DE)

(73) Assignee: BASF SE, Ludwigshafen (DE)

( * ) Notice: Subject to any disclaimer, the term of this patent is extended or adjusted under 35 U.S.C. 154(b) by 385 days.

(21) Appl. No.: 12/990,361

(22) PCT Filed: Apr. 30, 2009

(86) PCT No.: PCT/EP2009/055249
§ 371 (c)(1),
(2), (4) Date: Oct. 29, 2010

(87) PCT Pub. No.: WO2009/133166
PCT Pub. Date: Nov. 5, 2009

(65) Prior Publication Data
US 2011/0039698 A1    Feb. 17, 2011

(30) Foreign Application Priority Data

May 2, 2008  (EP) ..................... 08155572

(51) Int. Cl.
A01N 25/02    (2006.01)
A01N 43/56    (2006.01)
A01N 43/653   (2006.01)
A01N 25/04    (2006.01)

(52) U.S. Cl.
CPC ................................... A01N 25/04 (2013.01)

(58) Field of Classification Search
USPC ............... 504/116.1; 514/383, 407
See application file for complete search history.

(56) References Cited

U.S. PATENT DOCUMENTS 5,385,948 A * 1/1995 Chaudhuri ............ A01N 25/02
                                                504/234
5,911,915 A * 6/1999 Fonsny et al. ................ 424/405
2008/0185113 A1* 8/2008 Valls et al. .................... 162/75

FOREIGN PATENT DOCUMENTS

| EP | 0728414 | 8/1996 |
|---|---|---|
| EP | 1339281 | 6/2002 |
| EP | 1702607 | 9/2006 |
| FR | 2609631 | 7/1988 |
| FR | 2609631 A1 * | 7/1988 |
| JP | 2004-523491 | 8/2004 |
| RU | 2238649 | 10/2004 |
| WO | WO 9601305 | 1/1996 |
| WO | WO 02/45507 | 6/2002 |
| WO | WO 2002043488 | 6/2002 |
| WO | WO 2006/030006 | 3/2006 |
| WO | WO 2007110355 | 10/2007 |
| WO | WO 2008043807 | 4/2008 |

OTHER PUBLICATIONS

International Search Report, issued in PCT/EP2009/055249, dated Mar. 4, 2010.
International Preliminary Report on Patentability, issued in PCT/EP2009/055249, dated Aug. 9, 2010.
Rhee et al., "Formulation of Parenteral Microemulsion Containing Itraconazole," Pharm Res, vol. 30, No. 1, (2007), pp. 114-123.
Karakotov et al., "Tebuconazole-Based Fungicidal Composition," XP002498611.
Tomšičet al., "Ternary Systems of Nonionic Surfactant Brij 35, Water and Various Simple Alcohols: Structural Investigations by Small-Angle X-ray Scattering and Dynamic Light Scattering," Journal of Colloid and Interface Science, vol. 294, (2006), pp. 194-211.
Skelton et al., "Formulation of Pesticide Microemulsions," Pesticide Formulations, vol. 8, pp. 36-45, XP002053622.
Shell Chemicals, MSDS "Methyl Proxitol Acetate," (Mar. 16, 2007), XP007914204.

* cited by examiner

*Primary Examiner* — Johann R Richter
*Assistant Examiner* — Courtney Brown
(74) *Attorney, Agent, or Firm* — Brinks Gilson & Lione

(57) ABSTRACT

The present invention relates to a microemulsion comprising
(A) 0.1 to 50% by weight of at least one active ingredient,
(B) 0.5 to 40% by weight of at least one solvent which is fully miscible with water,
(C) 10 to 40% by weight of at least one nonionic surfactant,
(D) 0 to 10% by weight of further additives,
(E) 10 to 90% by weight of water and
(F) 0.1 to 60% by weight of at least one solvent which is partially miscible with water,

15 Claims, No Drawings

MICROEMULSION HAVING WIDE APPLICATION RANGE

This application is a National Stage application of International Application No. PCT/EP2009/055249, filed Apr. 30, 2009, the entire contents of which is hereby incorporated herein by reference. This application also claims priority under 35 U.S.C. § 119 to European Patent Application No. 08155572.4, filed May 2, 2008, the entire contents of which is hereby incorporated herein by reference.

The present invention relates to a microemulsion comprising at least one active ingredient, at least one polar solvent, optionally at least one unpolar solvent, at least one nonionic surfactant, optionally further additives, and water, the microemulsion not comprising any anionic surfactants, and to a process for the preparation of this microemulsion by mixing the individual components, until the use of this microemulsion for and to the treatment of plants.

Microemulsions comprising relevant active ingredients are already known from the prior art.

In general, a microemulsion is understood as meaning a clear, optically isotropic, liquid mixture of at least two fluids and at least one surface-active substance. There is a two-phase system, in contrast to micellar solutions, which are considered to be one phase. Microemulsions are thermodynamically stable dispersions of a fluid in another, stabilized by a layer of surface-active substance between the phases. The surface tension between the two phases is extremely low.

WO 2006/030006 A1 discloses a clear, water-based microemulsion comprising the antifungal reagent flutriafol and its use as a product for the treatment of seed. The microemulsion according to the abovementioned specification comprises, besides the active ingredient flutriafol, at least one fluid which is insoluble in water, and at least one anionic surface-active substance. Moreover, the microemulsion comprises at least one antifreeze agent selected from the group consisting of ethylene glycol, diethylene glycol, propylene glycol and mixtures of these. WO 2006/030006 A1 does not disclose any microemulsion which comprises an active ingredient and no anionic surface-active substances.

EP 0 728 414 A2 discloses a microemulsion comprising 3-isothiazolone compounds, a surface-active system comprising a nonionic surface-active substance and an anionic surface-active substance, and water. However, EP 0 728 414 A2 does not disclose any microemulsion which comprises an active ingredient and no anionic, surface-active substances.

A combination of nonionic and anionic surface-active substances in microemulsions which comprise an active ingredient and optionally at least one insecticide are also disclosed in WO 2007/017040 A2. However, this specification does not disclose any microemulsions which comprise no anionic surface-active substances.

EP 1 339 281 B1 discloses a microemulsion formulation comprising insecticides. Besides the insecticides, these microemulsions comprise at least one solvent selected from the group consisting of esters of aliphatic monocarboxylic acids, esters of aliphatic dicarboxylic acids, esters of aromatic monocarboxylic acids, esters of aromatic dicarboxylic acids and tri-n-alkyl phosphates, an emulsifier system comprising at least one anionic, surface-active substance and two or more nonionic, surface-active substances, further additives and water. Likewise, EP 1 339 281 B1 does not disclose any microemulsions which comprise active ingredients, but no anionic, surface-active substances.

Accordingly, it is an object of the present invention to provide a microemulsion which comprises at least one active ingredient and which is suitable for a series of different applications. It should be soluble even in a small amount of water, and it should be stable over a sufficiently long period of time, i.e. the microemulsion should remain clear. Furthermore, it is intended to avoid the disadvantage of anionic surfactants which are not suitable for certain applications. Furthermore, the microemulsion according to the invention is intended to be well suited to spray applications and to applications on plants.

These objects are achieved by a microemulsion comprising (A) 0.1 to 50% by weight of at least one active ingredient as component A,
(B) 0.5 to 40% by weight of at least one solvent which is fully miscible with water, being chosen from the group consisting of esters of acetic acid, of lactic acid, of benzoic acid, of dicarboxylic acids, cyclic esters, cyclic amides, carbonates, sulphur containing solvents, phosphates, ethers and mixtures thereof, as component B,
(C) 10 to 40% by weight of at least one nonionic surfactant as component C,
(D) 0 to 10% by weight of further additives as component D,
(E) 10 to 90% by weight of water as component E and
(F) 0.1 to 60% by weight of at least one solvent which is partially miscible with water, as component F, in each case based on the total microemulsion, where the total of the amounts of components A, B, C, D, E and F is 100% by weight and where the microemulsion does not comprise any anionic surfactants.

The object is also achieved by a process for the preparation of such a microemulsion, in which components A, B, C, E, F and, if appropriate, D are mixed with one another.

The object of the invention is also achieved by using the microemulsion according to the invention in the treatment of plants.

The individual components of the microemulsion according to the invention are described in detail in the following text:

Component A:

The microemulsion according to the invention comprises 0.1 to 50% by weight, preferably 0.1 to 20% by weight, especially preferably 2 to 10% by weight, of at least one active ingredient as component A. All those active ingredients which are known to the skilled worker for use in plant protection are suitable according to the invention as component A.

The at least one active ingredient which is present in the microemulsion according to the present invention is, for example, selected from pesticides, especially preferably selected from the group consisting of fungicides, insecticides, nematicides, herbicides, growth regulators and mixtures of these. Such pesticides are known to the skilled worker and are described, for example, in "The Pesticide Manual, 13th Ed. (2003), The British Crop Protection Council, London".

Suitable insecticides are, for example, selected from the group consisting of:

A.1. organo(thio)phosphates: acephate, azamethiphos, azinphos-methyl, chlorpyrifos, chlorpyrifos-methyl, chlorfenvinphos, diazinon, dichlorvos, dicrotophos, dimethoate, disulfoton, ethion, fenitrothion, fenthion, isoxathion, malathion, methamidophos, methidathion, methyl-parathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprophos, tetrachlorvinphos, terbufos, triazophos, trichlorfon;

A.2. carbamates: alanycarb, aldicarb, bendiocarb, benfuracarb, carbaryl, carbofuran, carbosulfan, fenoxycarb, furathiocarb, methiocarb, methomyl, oxamyl, pirimicarb, propoxur, thiodicarb, triazamate;

A.3. pyrethroids: allethrin, bifenthrin, cyfluthrin, cyhalothrin, cyphenothrin, cypermethrin, alpha-cypermethrin, beta-cypermethrin, zeta-cypermethrin, deltamethrin, esfenvalerate, etofenprox, fenpropathrin, fenvalerate, imiprothrin, lambda-cyhalothrin, gamma-cyhalothrin, permethrin, prallethrin, pyrethrin I and II, resmethrin, silafluofen, tau-fluvalinate, tefluthrin, tetramethrin, tralomethrin, transfluthrin, profluthrin, dimefluthrin;

A.4. growth regulators: a) chitin synthesis inhibitors: benzoylureas: chlorofluazuron, diflubenzuron, flucycloxuron, flufenoxuron, hexaflumuron, lufenuron, novaluron, teflubenzuron, triflumuron; buprofezin, diofenolan, hexythiazox, etoxazole, clofentazine; b) ecdysone antagonists: halofenozide, methoxyfenozide, tebufenozide, azadirachtin; c) juvenoids: pyriproxyfen, methoprene, fenoxycarb; d) lipid biosynthesis inhibitors: spirodiclofen, spiromesifen, spirotetramate;

A.5. nicotine receptor agonists/antagonists: clothianidin, dinotefuran, imidacloprid, thiamethoxam, nitenpyram, acetamiprid, thiacloprid; the thiazole compound of the formula (I)

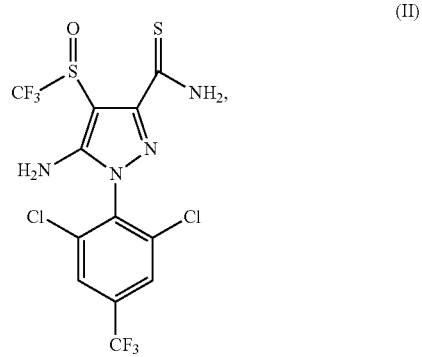 [SMILES: NC(=S)c1nn(-c2c(Cl)cc(C(F)(F)F)cc2Cl)c(N)c1S(=O)C(F)(F)F]

(I)

A.6. GABA antagonists: acetoprole, endosulfan, ethiprole, fipronil, vaniliprole, pyrafluprole, pyriprole, the phenylpyrazole compound of the formula (II)

(II)

A.7. macrocyclic lactone insecticides: abamectin, emamectin, milbemectin, lepimectin, spinosad, the compound of the formula (III) (CAS No. 187166-40-1)

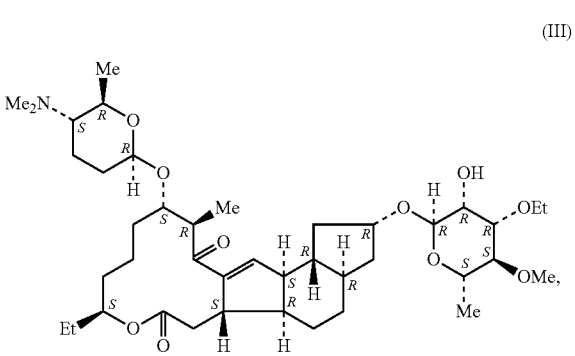

(III)

A.8. METI I substances: fenazaquin, pyridaben, tebufenpyrad, tolfenpyrad, flufenerim;
A.9. METI II and III substances: acequinocyl, fluacyprim, hydramethylnon;
A.10. uncouplers: chlorfenapyr;
A.11. oxidative phosphorylation inhibitors: cyhexatin, diafenthiuron, fenbutatin oxide, propargite;
A.12. molting inhibitors: cyromazine;
A.13. mixed function oxidase inhibitors: piperonyl butoxylate;
A.14. sodium channel blockers: indoxacarb, metaflumizone,
A.15. various: benclothiaz, bifenazate, cartap, flonicamid, pyridalyl, pymetrozine, sulfur, thiocyclam, flubendiamide, chlorantraniliprole, cyenopyrafen, flupyrazofos, cyflumetofen, amidoflumet, the aminoquinazolinone compound of the formula (IV)

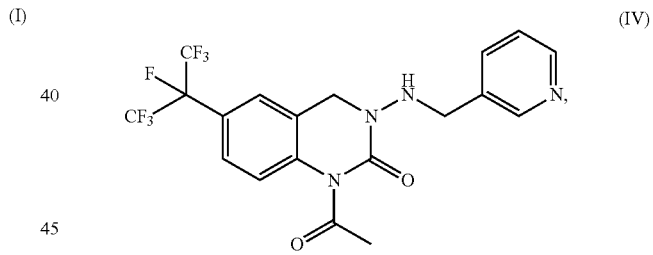

(IV)

N—R'-2,2-dihalo-1-R"cyclo-propanecarboxamide-2-(2,6-dichloro-α,α,α-tri-fluoro-p-tolyl)hydrazone or N—R'-2,2-di(R")propionamide-2-(2,6-dichloro-α,α,α-trifluoro-p-tolyl)-hydrazone, in which R' is methyl or ethyl, halo is chloro or bromo, R" is hydrogen or methyl, and R''' is methyl or ethyl, anthranilamide compounds of the formula (V)

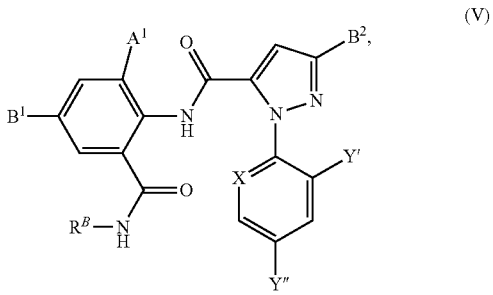

(V)

in which $A^1$ is $CH_3$, Cl, Br or I, X is C—H, C—Cl, C—F or N, Y' is F, Cl or Br, Y" is H, F, Cl or $CF_3$, $B^1$ is hydrogen, Cl, Br, I or CN, $B^2$ is Cl, Br, $CF_3$, $OCH_2CF_3$ or $OCF_2H$, and RB is hydrogen, $CH_3$ or $CH(CH_3)_2$, and malonitrile compounds as described in JP 2002 284608, WO 02/89579, WO 02/90320, WO 02/90321, WO 04/06677, WO 04/20399, JP 2004 99597, WO 05/68423, WO 05/68432 or WO 05/63694, preferably the malonitrile compounds $CF_3(CH_2)_2C(CN)_2CH_2(CF_2)_3CF_2H$, $CF_3(CH_2)_2C(CN)_2CH_2(CF_2)_5CF_2H$, $CF_3(CH_2)_2C(CN)_2(CH_2)_2C(CF_3)_2F$, $CF_3(CH_2)_2C(CN)_2(CH_2)_2(CF_2)_3CF_3$, $CF_2H(CF_2)_3CH_2C(CN)_2CH_2(CF_2)_3CF_2H$, $CF_3(CH_2)_2C(CN)_2CH_2(CF_2)_3CF_3$, $CF_3(CF_2)_2CH_2C(CN)_2CH_2(CF_2)_3CF_2H$, and $CF_3CF_2CH_2C(CN)_2CH_2(CF_2)_3CF_2H$.

The commercially available compounds of group A are described for example in "The Pesticide Manual, 13th Edition, British Crop Protection Council (2003) among other publications. Thioamides of the formula (II) and their preparation are described in WO 98/28279. Lepimectin is known from "Agro Project, PJB Publications Ltd, November 2004". Benclothiaz and its preparation are described in EP-A1 454621. Methidathion and paraoxon and their preparations are described in "Farm Chemicals Handbook, Volume 88, Meister Publishing Company, 2001." Acetoprole and its preparation are described in WO 98/28277. Metaflumizone and its preparation are described in EP-A1 462 456. Flupyrazofos is described in "Pesticide Science 54, 1988, pages 237-243" and in U.S. Pat. No. 4,822,779. Pyrafluprole and its preparation are described in JP 2002193709 and WO 01/00614. Pyriprole and its preparation are described in WO 98/45274 and U.S. Pat. No. 6,335,357. Amidoflumet and its preparation are described in U.S. Pat. No. 6,221,890 and JP 21010907. Flufenerim and its preparation are described in WO 03/007717 and WO 03/007718. Cyflumetofen and its preparation are described in WO 04/080180. Anthranilamides of the formula (V) and their preparation are described in WO 01/70671; WO 02/48137; WO 03/24222, WO 03/15518, WO 04/67528; WO 04/33468; and WO 05/118552. The malonitrile compounds $CF_3(CH_2)_2C(CN)_2CH_2(CF_2)_3CF_2H$, $CF_3(CH_2)_2C(CN)_2CH_2(CF_2)_5CF_2H$, $CF_3(CH_2)_2C(CN)_2(CH_2)_2C(CF_3)_2F$, $CF_3(CH_2)_2C(CN)_2(CF_2)_2(CF_2)_3CF_3$, $CF_2H(CF_2)_3CH_2C(CN)_2CH_2(CF_2)_3CF_2H$, $CF_3(CH_2)_2C(CN)_2CH_2(CF_2)_3CF_3$, $CF_3(CF_2)_2CH_2C(CN)_2CH_2(CF_2)_3CF_2H$ and $CF_3CF_2CH_2C(CN)_2CH_2(CF_2)_3CF_2H$ are described in WO 05/63694.

The fungicide may be selected from the group consisting of 1. strobilurins such as azoxystrobin, dimoxystrobin, enestroburin, fluoxastrobin, kresoxim-methyl, metominostrobin, picoxystrobin, pyraclostrobin, trifloxystrobin, orysastrobin, methyl (2-chloro-5-[1-(3-methylbenzyloxyimino)ethyl]-benzyl)carbamate, methyl (2-chloro-5-[1-(6-methylpyridin-2-ylmethoxy-imino)ethyl]benzyl)carbamate, methyl 2-(ortho-((2,5-dimethylphenyl-oxymethylene)phenyl)-3-methoxyacrylate;
2. carboxamides such as carboxanilides: benalaxyl, benodanil, boscalid, bixafen, carboxin, ethaboxam, mepronil, fenfuram, fenhexamid, flutolanil, furametpyr, metalaxyl, ofurace, oxadixyl, oxycarboxin, penthiopyrad, thifluzamide, tiadinil, N-(4'-bromobiphenyl-2-yl)-4-difluoromethyl-2-methylthiazole-5-carboxamide, N-(4'-trifluoromethylbiphenyl-2-yl)-4-difluoromethyl-2-methylthiazole-5-carboxamide, N-(4'-chloro-3'-fluorobiphenyl-2-yl)-4-difluoromethyl-2-methylthiazole-5-carboxamide, N-(3', 4'-dichloro-4-fluorobiphenyl-2-yl)-3-difluoromethyl-1-methylpyrazole-4-carboxamide, N-(2-cyanophenyl)-3,4-dichloroisothiazole-5-carboxamide, N-(3',4',5'-trifluorobiphenyl-2-yl)-3-difluoromethyl-1-methyl-1H-pyrazole-4-carboxamide, N-[2-(4'-trifluoromethylthio)biphenyl]-3-difluoromethyl-1-methyl-1H-pyrazole-4-carboxamide, N-[2-(1,3-dimethylbutyl)-phenyl]-1,3-dimethyl-5-fluoro-1H-pyrazole-4-carboxamide, N-(2-bicyclopropyl-2-yl-phenyl)-3-difluoromethyl-1-methyl-1H-pyrazole-4-carboxamide, N-(cis-2-bicyclopropyl-2-yl-phenyl)-3-difluoromethyl-1-methyl-1H-pyrazole-4-carboxamide, N-(trans-2-bicyclopropyl-2-yl-phenyl)-3-difluoromethyl-1-methyl-1H-pyrazole-4-carboxamide, N-[1,2,3,4-tetrahydro-9-(1-methylethyl)-1,4-methanonaphthalen-5-yl]-3-(difluoromethyl)-1-methyl-1H-pyrazole-4-carboxamide;
   carboxylic acid morpholides: dimethomorph, flumorph;
   benzamides: flumetover, fluopicolide (picobenzamid), zoxamid;
   other carboxamides: carpropamid, diclocymet, mandipropamid, N-(2-(4-[3-(4-chlorophenyl)prop-2-ynyloxy]-3-methoxyphenyl)ethyl)-2-methanesulfonylamino-3-methylbutyramide, N-(2-(4-[3-(4-chlorophenyl)prop-2-ynyloxy]-3-methoxyphenyl)ethyl)-2-ethanesulfonylamino-3-methylbutyramide;
3. azoles such as triazoles: bitertanol, bromuconazole, cyproconazole, difenoconazole, diniconazole, enilconazole, epoxyconazole, fenbuconazole, flusilazole, fluquinconazole, flutriafol, hexaconazole, imibenconazole, ipconazole, metconazole, myclobutanil, penconazole, propiconazole, prothioconazole, simeconazole, tebuconazole, tetraconazole, triadimenol, triadimefon, triticonazole; imidazoles: cyazofamid, imazalil, pefurazoate, prochloraz, triflumizole; benzimidazoles: benomyl, carbendazim, fuberidazole, thiabendazole; others: ethaboxam, etridiazole, hymexazole;
4. nitrogen-comprising heterocyclic compounds such as pyridines: fluazinam, pyrifenox, 3-[5-(4-chlorophenyl)-2, 3-dimethylisoxazolidin-3-yl]pyridine; pyrimidines: bupirimate, cyprodinil, ferimzone, fenarimol, mepanipyrim, nuarimol, pyrimethanil; piperazines: triforine; pyrroles: fludioxonil, fenpiclonil; morpholines: aldimorph, dodemorph, fenpropimorph, tridemorph; dicarboximides: iprodion, procymidone, vinclozolin; others: acibenzolar-5-methyl, anilazine, captan, captafol, dazomet, diclomezine, fenoxanil, folpet, fenpropidin, famoxadone, fenamidone, octhilinone, probenazole, proquinazide, pyroquilon, quinoxyfen, tricyclazol, 5-chloro-7-(4-methylpiperidin-1-yl)-6-(2,4,6-trifluorophenyl)-[1,2,4]triazolo[1,5-a]pyrimidine, 2-butoxy-6-iodo-3-propylchromen-4-one, N,N-dimethyl-3-(3-bromo-6-fluoro-2-methylindole-1-sulfonyl)-[1,2,4]triazole-1-sulfonamide;
5. carbamates and dithiocarbamates such as dithiocarbamates: ferbam, mancozeb, maneb, metiram, metam, propineb, thiram, zineb, ziram; carbamates: diethofencarb, flubenthiavalicarb, iprovalicarb, propamocarb, methyl 3-(4-chlorophenyl)-3-(2-isopropoxycarbonylamino-3-methylbutyrylamino)propionate, 4-fluorophenyl-N-(1-(1-(4-cyanophenyl)ethanesulfonyl)but-2-yl) carbamate;
6. other fungicides such as guanidines: dodine, iminoctadine, guazatine; antibiotics: kasugamycin, polyoxins, streptomycin, validamycin A; organometallic compounds: fentin salts; sulfur comprising heterocyclic compounds: isoprothiolane, dithianon; organophosphorus compounds: edifenphos, fosetyl, fosetyl-aluminum, iprobenfos, pyrazophos, tolclofos-methyl, phosphorous acid and its salts; organochlorine compounds: thiophanate-methyl, chlorothalonil, dichlofluanid, tolylfluanid, flusulfamid, phthalide, hexachlorobenzene, pencycuron, quintozene; nitrophenyl derivatives: binapacryl, dinocap, dinobuton; inorganic active compounds: Bordeaux mixture, copper acetate, copper hydroxide, copper oxychloride, basic copper sulfate, sulfur; others: spiroxamine, cyflufenamid, cymoxanil, metrafenon.

The herbicide is, for example, selected from the group consisting of:

b1) lipid biosynthesis inhibitors such as chlorazifop, clodinafop, clofop, cyhalofop, diclofop, fenoxaprop, fenoxaprop-p, fenthiaprop, fluazifop, fluazifop-P, haloxyfop, haloxyfop-P, isoxapyrifop, metamifop, propaquizafop, quizalofop, quizalofop-P, trifop, alloxydim, butroxydim, clethodim, cloproxydim, cycloxydim, profoxydim, sethoxydim, tepraloxydim, tralkoxydim, butylate, cycloate, di-allate, dimepiperate, EPTC, esprocarb, ethiolate, isopolinate, methiobencarb, molinate, orbencarb, pebulate, prosulfocarb, suif-allate, thiobencarb, thiocarbazil, tri-allate, vernolate, benfuresate, ethofumesate and bensulide';

b2) ALS inhibitors such as amidosulfuron, azimsulfuron, bensulfuron, chlorimuron, chlorsulfuron, cinosulfuron, cyclosulfamuron, ethametsulfuron, ethoxysulfuron, flazasulfuron, flupyrsulfuron, foramsulfuron, halosulfuron, imazosulfuron, iodosulfuron, mesosulfuron, metsulfuron, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, imazamethabenz, imazamox, imazapic, imazapyr, imazaquin, imazethapyr, cloransulam, diclosulam, florasulam, flumetsulam, metosulam, penoxsulam, bispyribac, pyriminobac, propoxycarbazone, flucarbazone, pyribenzoxim, pyriftalide and pyrithiobac;

b3) photosynthesis inhibitors such as atraton, atrazine, ametryn, aziprotryn, cyanazine, cyanatryn, chiorazine, cyprazine, desmetryn, dimethametryn, dipropetryn, eglinazine, ipazine, mesoprazine, methometon, methoprotryn, procyazine, proglinazine, prometon, prometryn, propazine, sebuthylazine, secbumeton, simazine, simeton, simetryn, terbumeton, terbuthylazine, terbutryn, trietazine, ametridione, amibuzin, hexazinon, isomethiozin, metamitron, metribuzin, bromacil, isocil, lenacil, terbacil, brompyrazon, chloridazon, dimidazon, desmedipham, phenisopham, phenmedipham, phenmedipham-ethyl, benzthiazuron, buthiuron, ethidimuron, isouron, methabenzthiazuron, monoisouron, tebuthiuron, thiazafluoron, anisuron, buturon, chlorbromuron, chloreturon, chlorotoluron, chloroxuron, difenoxuron, dimefuron, diuron, fenuron, fluometuron, fluothiuron, isoproturon, linuron, methiuron, metobenzuron, metobromuron, metoxuron, monolinuron, monuron, neburon, parafluoron, phenobenzuron, siduron, tetrafluoron, thidiazuron, cyperquat, diethamquat, difenzoquat, diquat, morfamquat, paraquat, bromobonil, bromoxynil, chloroxynil, iodobonil, ioxynil, amicarbazon, bromofenoxim, flumezin, methazol, bentazone, propanil, pentanochlor, pyridate and pyridafol;

b4) protoporphyrinogen IX oxidase inhibitors such as acifluorfen, bifenox, chlomethoxyfen, chiornitrofen, ethoxyfen, fluorodifen, fluoroglycofen, fluoronitrofen, fomesafen, furyloxyfen, halosafen, lactofen, nitrofen, nitrofluorfen, oxyfluorfen, fluazolate, pyraflufen, cinidonethyl, flumiclorac, flumioxazin, flumipropyn, fluthiacet, thidiazimin, oxadiazon, oxadiargyl, azafenidin, carfentrazone, sulfentrazone, pentoxazone, benzfendizone, butafenacil, pyraclonil, profluazol, flufenpyr, flupropacil, nipyraclofen and etnipromid;

b5) bleacher herbicides such as metflurazon, norflurazon, flufenican, diflufenican, picolinafen, beflubutamid, fluridone, fluorochloridone, flurtamone, mesotrione, sulcotrione, isoxachlortole, isoxaflutole, benzofenap, pyrazolynate, pyrazoxyfen, benzobicyclon, amitrole, clomazone, aclonifen, 4-(3-trifluoromethylphenoxy)-2-(4-trifluoromethylphenyl)pyrimidine and 3-heterocyclyl-substituted benzoyl derivatives of the formula VI, see, for example, WO 96/26202, WO 97/41116, WO 97/41117 and WO 97/41118

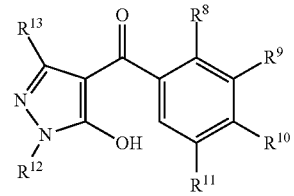

(VI)

in which the variables $R^8$ to $R^{13}$ are defined as follows:

$R^8$, $R^{10}$ independently of one another are hydrogen, halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-alkylsulfinyl or $C_1$-$C_6$-alkylsulfonyl;

$R^9$ is a heterocyclic radical selected from the group consisting of thiazol-2-yl, thiazol-4-yl, thiazol-5-yl, isoxazol-3-yl, isoxazol-4-yl, isoxazol-5-yl, 4,5-dihydroisoxazol-3-yl, 4,5-dihydroisoxazol-4-yl and 4,5-dihydroisoxazol-5-yl, where the abovementioned radicals may be unsubstituted or mono- or polysubstituted, i.e. mono-, di-, tri- or tetrasubstituted by halogen, $C_1$-$C_6$-alkyl, $C_1$-$C_4$-alkoxy, $C_1$-$C_4$-haloalkyl, $C_1$-$C_4$-haloalkoxy or $C_1$-$C_4$-alkylthio;

$R^{11}$ is hydrogen, halogen or $C_1$-$C_6$-alkyl;

$R^{12}$ is $C_1$-$C_6$-alkyl;

$R^{13}$ is hydrogen or $C_1$-$C_6$-alkyl.

b6) EPSP synthase inhibitors such as glyphosate;

b7) glutamine synthase inhibitors such as glufosinate and bilanaphos;

b8) DHP synthase inhibitors such as asulam;

b9) mitosis inhibitors such as benfluralin, butralin, dinitramine, ethalfluralin, fluchloralin, isopropalin, methalpropalin, nitralin, oryzalin, pendimethalin, prodiamine, profluralin, trifluralin, amiprofos-methyl, butamifos, dithiopyr, thiazopyr, propyzamide, tebutam, chlorthal, carbetamide, chlorbufam, chlorpropham and propham;

b10) VLCFA inhibitors such as acetochlor, alachlor, butachlor, butenachlor, delachlor, diethatyl, dimethachlor, dimethenamid, dimethenamid-P, metazachlor, metolachlor, S-metolachlor, pretilachlor, propachlor, propisochlor, prynachlor, terbuchlor, thenylchlor, xylachlor, allidochlor, CDEA, epronaz, diphenamid, napropamide, naproanilide, pethoxamid, flufenacet, mefenacet, fentrazamide, anilofos, piperophos, cafenstrole, indanofan and tridiphane;

b11) cellulose biosynthesis inhibitors such as dichlobenil, chlorthiamid, isoxaben and flupoxam;

b12) uncoupler herbicides such as dinofenate, dinoprop, dinosam, dinoseb, dinoterb, DNOC, etinofen and medinoterb;

b13) auxin herbicides such as clomeprop, 2,4-D, 2,4,5-T, MCPA, MCPA, thioethyl, dichlorprop, dichlorprop-P, mecoprop, mecoprop-P, 2,4-DB, MCPB, chloramben, dicamba, 2,3,6-TBA, tricamba, quinclorac, quinmerac, clopyralid, fluoroxypyr, picloram, triclopyr and benazolin;

b14) auxin transport inhibitors such as naptalam, diflufenzopyr;

b15) benzoylprop, flamprop, flamprop-M, bromobutide, chlorflurenol, cinmethylin, methyldymrone, etobenzanid, fosamine, metam, pyributicarb, oxaziclomefone, dazomet, triaziflam and methyl bromide.

Fungicides and insecticides are preferred.

Preferred insecticides are carbamates such as alanycarb, benfuracarb, carbaryl, carbosulfan, fenoxycarb, furathiocarb, indoxacarb, methiocarb, methomyl, oxamyl, pirimicarb, propoxur, thiodicarb or triazamate; pyrethroids such as bifenthrin, cyfluthrin, cypermethrin, alpha-cypermethrin, deltamethrin, esfenvalerate, ethofenprox, fenpropathrin, fenvalerate, cyhalothrin, lambda-cyhalothrin, permethrin, silafluofen, tau-fluvalinate, tefluthrin, tralomethrin or zeta-cypermethrin; arthropod growth regulators such as chitin synthesis inhibitors: benzoylureas: chlorfluazuron, diflubenzuron, flucycloxuron, flufenoxuron, hexaflumuron, lufenuron, novaluron, teflubenzuron, triflumuron; buprofezin, diofenolan, hexythiazox, etoxazole, clofentazine; ecdysone antagonists: halofenozide, methoxyfenozide, tebufenozide; juvenoids: pyriproxyfen, methoprene, fenoxycarb; lipid biosynthesis inhibitors: spirodiclofen; neonicotinoids such as acetamiprid, clothianidin, flonicamid, imidacloprid, nitenpyram, thiacloprid, thiamethoxam, dinetofuran; and ethiprole, fipronil, metaflumizone, N—R'-2,2-dihalo-1-R"cyclopropanecarboxamide 2-(2,6-dichloro-α,α,α-trifluoro-p-tolyl)hydrazone or N—R'-2,2-di(R''')propionamide 2-(2,6-dichloro-α,α,α-trifluoro-p-tolyl)hydrazono, where R' is methyl or ethyl, halo is chlorine or bromine, R" is hydrogen or methyl and R''' is methyl or ethyl, abamectin, acequinocyl, amitraz, azadirachtin, bifenazate, *Bacillus thuringiensis, Bacillus subtilis*, cartap, chlorfenapyr, chlordimeform, cyromazine, diafenthiuron, diofenolan, emamectin, endosulfan, fenazaquin, formetanate, formetanate hydrochloride, hydramethylnon, indoxacarb, 4-{(2Z)-2-({[4-(trifluoro-methoxy)anilino]carbonyl}hydrazono)-2-[3-(trifluoromethyl)phenyl]ethyl}benzonitrile, pyridaben, pyridalyl, pymetrozine, spinosad, sulfur, tebufenpyrad, and thiocyclam.

Especially preferred insecticides are fipronil, flufenoxuron, teflubenzuron, metaflumizone or alpha-cypermethrin, very especially preferred are fipronil, flufenoxuron or alpha-cypermethrin.

Preferred fungicides are epoxiconazole, pyraclostrobin, kresoxim-methyl, carbendazim, metrafenone, boscalid, triticonazole, metconazole, dimethomorph, fenpropimorph, prochloraz, vinclozolin, iprodione, dithianon, metiram, tebuconazol, azoxystrobin, mancozeb, trifloxystrobin, chlorothalonil, metalaxyl, fosetyl, difemoconazole, cyprodinil, spiroxamine, prothioconazole or picoxystrobin.

The at least one active ingredient employed as component A in the microemulsion according to the invention is very especially preferably selected from the group consisting of fipronil, metconazole, pyraclostrobin and mixtures of these.

Fipronil corresponds to the IUPAC nomenclature 5-amino-1-(2,6-dichloro-α,α,α-trifluoro-p-tolyl)-4-trifluoromethylsulfinylpyrazole-3-carbonitrile. Metconazole corresponds to the IUPAC nomenclature (1RS,5RS,1RS,5SR)-5-(4-chlorobenzyl)-2,2-dimethyl-1-(1H-1,2,4-triazol-1-ylmethyl)cyclopentanol. Pyraclostrobin corresponds to the IUPAC nomenclature methyl {2-[1-(4-chlorophenyl)pyrazol-3-yloxymethyl]phenyl}methoxy)carbamate.

The active ingredients which are present in accordance with the invention can be prepared by processes known to the skilled worker or are commercially available.

Component B:

As component B, the microemulsion according to the invention comprises 0.5 to 40% by weight, preferably 1.0 to 25% by weight, especially preferably 2.0 to 20% by weight, of at least one solvent which is fully miscible with water, being chosen from the group consisting of esters of acetic acid, of lactic acid, of benzoic acid, of dicarboxylic acids, cyclic esters, cyclic amides, carbonates, sulphur containing solvents, phosphates, ethers and mixtures thereof, as component B.

In a preferred embodiment, the micoemulsion according to the present invention, comprises at least one solvent which is fully miscible with water being selected from the group consisting of esters, for example esters of acetic acid, preferably 1-methoxy-2-propanol acetate, methyl-proxitol-acetate, propylene-glycol-monomethyl-ether-acetate (Arcosolv PMA), of lactic acid, preferably methyl lactate, ethyl lactate, n-propyl lactate, of benzoic acid, for example methyl benzoate, ethyl benzoate, propyl benzoate, of dicarboxylic acids such as glutaric acid, succinic acid or adipic acid, preferably dimethyl glutarate, dimethyl succinate and/or dimethyl adipate or a mixture of dimethyl glutarate, dimethyl succinate and dimethyl adipate (Rhodiasolv RPDE), diethyl glutarate, diethyl succinate and/or diethyl adipate, dipropyl glutarate, dipropyl succinate and/or dipropyl adipate, cyclic esters, for example gamma-butyrolactone, cyclic amides, preferably N-methylvalerolactame, N-ethylvalerolactame, N-propylvalerolactame, carbonates, for example propylene carbonate, butylene carbonate, sulfur-comprising solvents, for example dimethyl sulfoxide (DMSO), phosphates, for example tributylphosphate, tris-(2-ethylhexyl) phosphate, ethers, for example propylene-glycol-monophenyl-ether, and mixtures of these.

Within the scope of the present invention, "fully miscible with water" means that water and the at least one solvent which is employed as component B can, preferably at room temperature, be mixed with one another in any ratio to give one phase.

The at least one polar solvent which is employed as component B is especially preferably selected from the group consisting of 1-methoxy-2-propanol acetate, n-propyl lactate, gamma-butyrolactone, DMSO and mixtures of these.

It is preferred that the microemulsion according to the invention does not comprise any alcohol, diol and/or triol, i.e. that in the microemulsion according to the present invention, the amount of these solvents or compounds is preferably below the detection limit, for example less than 0.5% by weight, preferably less than 0.1% by weight, particularly preferred less than 0.01% by weight, in each case based on the whole microemulsion.

Component C:

As component C, the microemulsion according to the invention comprises 10 to 40% by weight, preferably 10 to 25% by weight, especially preferably 12 to 25% by weight, of at least one nonionic surfactant.

Nonionic surfactants which can be employed in accordance with the present invention are all those surface-active substances or compounds which form virtually no ions in an aqueous medium.

Suitable nonionic surfactants are known to the skilled worker, for example:

1. $C_2$-$C_{18}$-alkoxylates, in particular ethoxylates, propoxylates and/or butoxylates, of linear or branched $C_5$-$C_{25}$- alcohols, for example fatty alcohols, oxoalcohols, Guerbet alcohols, alcohols from the aluminum-catalyzed olefin oligomerization, alcohols from the ketone oligomerization, alcohols from the oxidation of hydrocarbons or alcohols from the hydration of olefins;

2. $C_2$-$C_{18}$-alkoxylates, in particular ethoxylates, propoxylates and/or butoxylates, of phenol or of phenols which are substituted in the nucleus, for example phenol ethoxylate, cresol ethoxylate, alkylphenol ethoxylate, tributylphenol ethoxylate or tristyrylphenol ethoxylate;
3. $C_2$-$C_{18}$-alkoxylates, in particular ethoxylates, propoxylates and/or butoxylates, of fats or other $C_8$-$C_{22}$-fatty acid esters, for example of castor oil ethoxylates, ethoxylates of partially hydrolyzed fats or ethoxylated fatty acid methyl esters;
4. $C_2$-$C_{18}$-alkoxylates, in particular ethoxylates, propoxylates and/or butoxylates, of $C_5$-$C_{25}$-alkylamines, in particular $C_8$-$C_{22}$-fatty amines;
5. $C_2$-$C_{18}$-alkoxylates, in particular ethoxylates, propoxylates and/or butoxylates, of $C_5$-$C_{25}$-carboxylic acids, for example oleic acid, erucic acid, isononanoic acid, isostearic acid, alkylsuccinic acid or adipic acid;
6. $C_2$-$C_{18}$-alkoxylates, in particular ethoxylates, propoxylates and/or butoxylates, of $C_5$-$C_{25}$-carboxamides, for example oleic acid amide or erucic acid amide;
7. crosslinked, preferably formaldehyde-crosslinked, alkylphenol alkoxylates, also known as "resin emulsifiers",
8. mixed polymers of a water-miscible $C_1$-$C_8$-starting alcohol, ethylene oxide and a higher $C_3$-$C_{18}$-alkylene oxide, preferably propylene oxide, of block structure or mixed structure. The starter here is typically water, a $C_1$-$C_4$-monoalcohol, a $C_2$-$C_6$-dialcohol, a $C_3$-$C_6$-trialcohol or a $C_4$-$C_6$-oligoalcohol. Examples of polymers are poloxamers, butanol/PO/EO block copolymers, alkoxylates of butanediol, of glycerol, of trimethylolpropane, of pentaerythritol or of sorbitol.
9. mixed polymers of a water-miscible $C_1$-$C_8$-starting amine, ethylene oxide and a higher $C_2$-$C_{18}$-alkylene oxide, preferably propylene oxide, of block structure or mixed structure. The starter here is typically ethylenediamine, diethylenetriamine or triethylenetetraamine. Examples of polymers are: poloxamer T;
10. $C_5$-$C_{25}$-alkylglucosides or —N-alkylglucamides and their alkoxylates;
11. $C_5$-$C_{25}$-carboxylic esters of sorbitol, of oligo- and of polyglycerol or of sorbitan and their alkoxylates with $C_2$-$C_{18}$-alkylene oxide, preferably ethylene oxide;
12. copolymers of glycerol and $C_5$-$C_{25}$-alcohols which can be prepared for example from alcohol and epichlorohydrin;
13. $C_1$-$C_{25}$-carboxylic esters with the structures given in 1. to 12, for example difatty acid esters of polyethylene oxide or carboxylic esters of alcohol alkoxylates;
14. $C_1$-$C_{18}$-ethers with the structures given in 1. to 12, for example methylated EO/PO block copolymers, or benzylated or tert-butylated alcohol alkoxylates;

with the proviso that they:
1) are surface-active; this can be determined readily as follows: a compound is surface-active when its 1% strength solution in water has a surface tension of no more than 60 mN/m, preferably no more than 50 mN/m, very especially preferably no more than 45 mN/m, and
2) dissociate into ions in a 1% strength solution in water to less than 5%.

Nonionic surfactants which can be employed in accordance with the present invention are all those surface-active substances or compounds which do not form ions in an aqueous medium. Suitable nonionic surfactants are known to the skilled worker.

Preferably, the at least one nonionic surfactant present in the microemulsion according to the invention is selected from the group consisting of compounds which are formed by alkoxylating compounds with at least one active hydrogen atom, alkoxylates of alkylphenols, block polymers of $C_2$-$C_6$-alkylene oxides, alkylglycosides and mixtures of these.

Preferred nonionic surfactants which are employed are water-soluble adducts obtained by the addition reaction of 3 to 30 mol of an alkylene oxide, preferably ethylene oxide or propylene oxide, and one mole of an organic hydrophobic, aliphatic or alkylaromatic compound with 8 to 24 carbon atoms and at least one reactive hydrogen atom, in particular a reactive hydroxyl, amino, amido or carboxyl group.

Examples of nonionic water-soluble adducts obtained by the addition reaction of several moles of an alkylene oxide with one mole of an organic hydrophobic compound are the following:

adducts of ethylene oxide and aliphatic, linear or branched, primary or secondary alcohols which have more than 8 carbon atoms and which are derived for example from tallow or coconut fatty acids, having 3 to 20 ethylene oxide groups, for example a $C_{1-3}$-alcohol ethoxylated with 1 to 15, preferably 5, 7, 11, 15 ethylene oxide units, adducts of ethylene oxide and alkylphenols in which the phenols may be mono- or polyalkylated and the total number of carbon atoms in the side chain(s) is 5 to 18, specific examples being adducts of one mole of nonylphenol and 8 to 15 moles of ethylene oxide or polyoxyethylene tristyrylphenol ether, adducts of ethylene oxide and fatty acid esters, preferably monofatty acid esters of the sugar alcohols sorbitol and mannitol, polyglycol oxycarboxylic acid esters obtained by reacting ethylene oxide with carboxylic acids, the latter being natural fatty acids or synthetic fatty acids from oxidized paraffin wax with 8 to 20 carbon atoms or alkylbenzoic or naphthenic acids with 5 to 18 carbon atoms in the alkyl chain, the adducts of ethylene oxide and fatty acyl alkanolamides of the type $C_7$-$C_{17}$-alkyl-CO—NHC$_2$H$_4$OH, $C_7$-$C_{17}$-alkyl-CO—N—(C$_2$H$_4$OH)$_2$, the adducts of ethylene oxide and $C_8$-$C_{18}$-alkyl-, $C_8$-$C_{18}$-alkenyl- and $C_8$-$C_{18}$-alkyl-arylamines, and mixtures of the abovementioned nonionic surfactants.

In a preferred embodiment, the microemulsion according to the invention comprises at least one nonionic surfactant selected from the group consisting of a $C_{1-3}$-alcohol ethoxylated with 1 to 15, preferably 5, 7, 11, 15 ethylene oxide units, polyoxyethylene tristyrylphenol ether and mixtures of these.

In accordance with the invention, a nonionic surfactant or a mixture of two or more nonionic surfactants may be present in the microemulsion. It is preferred to employ a combination of two different nonionic surfactants. The weight ratio for the two nonionic surfactants can vary from 1:10 to 10:1.

In a preferred embodiment, the microemulsion according to the invention does not comprise any anionic surfactant. Within the context of the present invention, this means that the anionic surfactant content in the microemulsion according to the invention is 1% by weight, preferably ≤0.1% by weight, especially preferably 5-0.01% by weight, very especially preferably 0% by weight, in each case based on all of the microemulsion. Methods for determining this content are known to the skilled worker, for example gas chromatography or NMR spectroscopic methods.

Component D:

As component D, the microemulsion according to the invention comprises 0 to 10% by weight, preferably 0 to 5% by weight, of further additives. If further additives are present in the microemulsion according to the invention, these are preferably present in a concentration of from 0.5 to 10% by weight, preferably from 0.5 to 5% by weight, in the microemulsion according to the invention.

Preferred additives which are optionally present in the microemulsion according to the invention are known to the skilled worker. The additives are preferably selected from the group consisting of humectants, dispersants, further surface-active substances, with no anionic surface-active substances being added, inorganic salts, for example NaCl, $Na_2SO_4$, $MgCl_2$, oligo- or polyphosphates, carbonates such as, for example, calcium carbonate, fertilizers such as ammonium sulfate, ammonium nitrate, urea, phosphorus- and potassium-comprising compounds and, if appropriate, further trace elements, antifoams, binders, for example natural or synthetic substances such as polyamino acids, polyvinyl alcohols, polyvinylpyrrolidone, polyacrylic acid derivatives, polymers, colorants, for example for dressing seed, stabilizers, biocides and mixtures of these. If ready-to-use solutions are to be prepared, it is preferred to add an additive selected from among oils such as vegetable oils, high-boiling hydrocarbons such as kerosene or paraffin, and mixtures of these to the microemulsion according to the invention, with no anionic surface-active substances being added.

Suitable colorants are, for example, selected from the group consisting of Rhodamin B, C.I. Pigment Red 112, C.I. Solvent Red 1, Pigment Blue 15:4, Pigment Blue 15:3, Pigment Blue 15:2, Pigment Blue 15:1, Pigment Blue 80, Pigment Yellow 1, Pigment Yellow 13, Pigment Red 112, Pigment Red 48:2, Pigment Red 48:1, Pigment Red 57:1, Pigment Red 53:1, Pigment Orange 43, Pigment Orange 34, Pigment Orange 5, Pigment Green 36, Pigment Green 7, Pigment White 6, Pigment Brown 25, Basic Violet 10, Basic Violet 49, Acid Red 51, Acid Red 52, Acid Red 14, Acid Blue 9, Acid Yellow 23, Basic Red 10, Basic Red 108 and mixtures of these (names in accordance with Color Index).

As a further additive, the microemulsion according to the invention may also comprise preservatives, since water-based formulations are intended to be protected from contamination with microorganisms.

In an especially preferred embodiment, the microemulsion according to the invention is free from antifreeze agents, i.e. the antifreeze agent content is ≤1% by weight, preferably 5-0.1% by weight, especially preferably ≤0.01% by weight, as can be determined with the abovementioned methods.

Component E:

As component E, the microemulsion according to the invention comprises 10 to 90% by weight, preferably 10 to 50% by weight, especially preferably 10 to 40% by weight, of water. Since the water content in the microemulsion according to the invention is preferably low, the microemulsion according to the invention is preferably present in the form of a concentrate. In the context of the present application, a concentrate is understood as meaning a microemulsion with a water content of, for example, 10 to 20% by weight based on the microemulsion. If the microemulsion according to the invention is present in the form of a concentrate, the latter can be diluted by adding water, for example before the application. The present invention relates both to the concentrate and to the ready-to-use preparation prepared therefrom. For example, a ready-to-use preparation can be prepared from the microemulsion according to the invention by mixing for example 0.01 to 0.10% by weight, preferably 0.03 to 0.08% by weight, for example 0.05% by weight, of the microemulsion according to the invention with the corresponding amount of water. The concentration of the ready-to-use preparation will here depend on the desired application.

In the context of the present invention, water is, firstly, pure water which has been freed from impurities for example by distillative methods. Fully demineralized water may also be employed in accordance with the invention. However, it is additionally also possible to employ water of drinking-water quality. This means that the drinking water employed comprises conventional impurities in conventional amounts. It is especially preferred to employ fully demineralized water in the microemulsion according to the invention.

Component F:

As component F, the microemulsion according to the invention comprises 0.1 to 60% by weight of at least one solvent which is partially miscible with water.

As component F, the microemulsion according to the invention comprises 0.1 to 60% by weight, preferably 5 to 58% by weight, especially preferably 20 to 55% by weight, of at least one solvent which is partially miscible with water.

Within the scope of the present invention, "a solvent which is partially miscible with water" means that this solvent can be mixed with water in an amount of from 0.1 to 10% by weight, with only one phase developing. At amounts over 10% by weight, two phases develop.

The at least one solvent which is partially miscible with water which can be employed takes the form of all solvents which are known to the skilled worker, are suitable for use in microemulsions and have a solubility in water of from 0.1 to 10% by weight.

In a preferred embodiment, the at least one solvent which is partially miscible with water is selected from the group consisting of benzyl alcohol, di-$C_1$-$C_4$-alkylamides of fatty acids with 6 to 16 carbon atoms, linear or cyclic ketones, for example 2-heptanone, 3-heptanone, 4-heptanone, acetophenone, cyclohexanone, phosphates, for example tri-$C_1$-$C_6$-alkyl phosphate, preferably tributyl phosphate and mixtures thereof, especially preferably a mixture of C8/C10-fatty acid dimethylamides or cyclohexanone, 2-heptanone, acetophenone, tributyl phosphate.

The total of the amounts of components A, B, C, optionally D, E and F which are present in the microemulsion according to the invention is 100% by weight.

In a preferred embodiment, the microemulsion according to the invention consists of components A, B, C, E and F, i.e. no further substances are present in the microemulsion.

The present invention also relates to a process for the preparation of the microemulsion according to the invention, where components A, B, C, optionally D, E and F are mixed, preferably in the suitable amounts.

Mixing can be effected by methods known to the skilled worker. For example, the individual components are dissolved or emulsified, preferably at room temperature. If further adjuvants and additives are present, they are preferably also added at room temperature. In general, the individual components can be mixed with one another in any feasible sequence.

In a preferred embodiment of the process according to the invention, components B and F are first mixed in the relevant amounts. Thereafter, the relevant amount of component A is added, and the mixture is preferably stirred until a solution is formed. Thereafter, component C and any additives which may be present (component D) are added. Finally, the relevant amount of water (component E) is added in order to arrive at the microemulsion according to the invention. The individual additions and the stirring in order to arrive at solutions are carried out by procedures known to the skilled worker, for example in reactors made of glass or metal in which suitable devices, for example stirrer bars or stirrer blades are present. The individual components are mixed at a temperature of from 0 to 50° C., preferably at ambient temperature.

The microemulsions according to the invention are distinguished by a particularly high storage stability; for example, the microemulsions according to the invention are stable for at least one week at a temperature of 0° C. and for at least two weeks at a temperature of 54° C. Moreover, the microemulsion according to the invention is soluble even in a small amount of water and compatible with the customary tank mix adjuvants known to the skilled worker. This is why the microemulsions according to the invention are particularly suitable for the treatment of plants.

The present invention also relates to the use of the microemulsion according to the invention for the treatment of plants, trees, the soil or seed, preferably against insects, nematodes, fungi or weeds, more preferably in the crop or non-crop sector.

In a preferred embodiment, the microemulsion according to the invention is present as a dilute aqueous solution upon use.

Crop use means that parts of the plants are treated from the outside with the microemulsion according to the invention. Non-crop use means that the plant is treated with the microemulsion according to the invention for example from the inside. Moreover, the treatment may be carried out on plants which are still located in the soil, i.e. beneath the surface (pre-emergence) or which are located above the soil (post-emergence).

In the treatment of plants, the microemulsion according to the invention can preferably be used as follows.

Treatment of the leaves of a plant by spraying the leaves with a dilute aqueous solution of the microemulsion according to the invention (crop post-emergence application)

Treatment of the soil with a dilute aqueous solution of the microemulsion according to the invention (crop pre-emergence application)

Treatment of the seed with the microemulsion according to the invention or with a dilute aqueous solution of the microemulsion according to the invention (crop application)

Injecting the microemulsion according to the invention or a dilute aqueous solution of the microemulsion according to the invention into the stem or the stalk of a plant (non-crop post-emergence application), for example for controlling tree-dwelling insects, application of the microemulsion according to the invention or of a dilute aqueous solution of the microemulsion according to the invention to and into the arable soil, for example for controlling insects such as termites, ants (non-crop application) before the seed is sown.

Procedures for applying such a microemulsion to the plants to be treated, for example by spraying, are known to the skilled worker.

EXAMPLES

Example 1

The tables which follow list microemulsions (ME) 1 to 16 according to the invention. The quantities are given in grams. Knowing the total, the skilled worker knows how the percentages by weight of the individual components can be determined. The individual microemulsions are prepared by combining the individual components at room temperature. The fipronil employed has a purity of 88.91%, the metconazole employed a purity of 99%. Tables 1 and 2 describe microemulsions according to the invention with fipronil as active ingredient. Table 3 mentions microemulsions according to the invention with metconazole as active ingredient.

TABLE 1

Microemulsions 1 to 5 with fipronil as active ingredient

| | ME serial No. | | | | |
|---|---|---|---|---|---|
| | 1 | 2 | 3 | 4 | 5 |
| Fipronil | 56.24 | 56.24 | 56.24 | 56.24 | 56.24 |
| 2-Heptanone | 105.0 | — | — | — | — |
| 1-Methoxy-2-propanol acetate | — | 105.0 | 105.0 | — | — |
| Cyclohexanone | — | — | — | 105.0 | 105.0 |
| n-Propyl lactate | — | — | — | — | — |
| Tributyl phosphate | — | — | — | — | — |
| gamma-Butyrolactone | — | — | — | — | — |
| DMSO | 25.0 | 25.0 | 25.0 | 25.0 | 25.0 |
| C8/C10-Diamide | — | — | — | — | — |
| Mixture of C8/C10-fatty acid dimethylamides | 425.0 | 425.0 | 425.0 | 425.0 | 425.0 |
| Polyoxyethylene tristyrylphenyl ether | 160.0 | 180.0 | 180.0 | 140.0 | 180.0 |
| C13 Oxoalcohol 5 EO | 40.0 | 20.0 | — | 60.0 | — |
| C13 Oxoalcohol 7 EO | — | — | 20.0 | — | 20.0 |
| C13 Oxoalcohol 6 EO | — | — | — | — | — |
| Distilled H$_2$O | 189.0 | 189.0 | 189.0 | 189.0 | 189.0 |
| Total | 1000.2 | 1000.2 | 1000.2 | 1000.2 | 1000.2 |

TABLE 2

Microemulsions 6 to 10 with fipronil as active ingredient

| | ME serial No. | | | | |
|---|---|---|---|---|---|
| | 6 | 7 | 8 | 9 | 10 |
| Fipronil | 56.24 | 56.24 | 56.24 | 56.24 | 56.24 |
| 2-Heptanone | — | — | — | — | — |
| 1-Methoxy-2-propanol acetate | — | — | — | — | — |
| Cyclohexanone | — | — | — | — | — |
| n-Propyl lactate | 105.0 | 105.0 | — | — | — |
| Tributyl phosphate | — | — | 105.0 | — | — |
| gamma-Butyrolactone | — | — | — | 105.0 | 105.0 |
| DMSO | 25.0 | 25.0 | 25.0 | 25.0 | 25.0 |
| Mixture of C8/C10-fatty acid dimethylamides | 425.0 | 425.0 | 425.0 | 425.0 | 425.0 |
| Polyoxyethylene tristyrylphenyl ether | 160.0 | 160.0 | 190.0 | 190.0 | 190.0 |

TABLE 2-continued

Microemulsions 6 to 10 with fipronil as active ingredient

| | ME serial No. | | | | |
|---|---|---|---|---|---|
| | 6 | 7 | 8 | 9 | 10 |
| C13 Oxoalcohol 5 EO | 40.0 | — | — | 10.0 | — |
| C13 Oxoalcohol 7 EO | — | 40.0 | — | — | 10.0 |
| C13 Oxoalcohol 6 EO | — | — | 10.0 | — | — |
| Distilled H$_2$O | 189.0 | 189.0 | 189.0 | 189.0 | 189.0 |
| Total | 1000.2 | 1000.2 | 1000.2 | 1000.2 | 1000.2 |

TABLE 3

Microemulsions 11 to 16 with metconazole as active ingredient

| | ME serial No. | | | | | |
|---|---|---|---|---|---|---|
| | 11 | 12 | 13 | 14 | 15 | 16 |
| Metconazole | 50.5 | 50.5 | 50.5 | 50.5 | 50.5 | 50.5 |
| Benzyl alcohol | 150.0 | — | — | 150.0 | — | — |
| Cyclohexanone | — | 150.0 | — | — | 150.0 | — |
| 1-Methoxy-2-propanol acetate | — | — | 150.0 | — | — | 150.0 |
| n-Propyl lactate | — | — | — | 50.0 | 50.0 | 50.0 |
| DMSO | 50.0 | 50.0 | 50.0 | — | — | — |
| Mixture of C8/C10-fatty acid dimethylamides | 300.0 | 300.0 | 300.0 | 300.0 | 300.0 | 300.0 |
| Polyoxyethylene tristyrylphenyl ether | 180.0 | 200.0 | 200.0 | 180.0 | 200.0 | 200.0 |
| C13 Oxoalcohol 5 EO | 20.0 | — | — | 20.0 | — | — |
| Distilled H$_2$O | 249.5 | 249.5 | 249.5 | 249.5 | 249.5 | 249.5 |
| Total | 1000.0 | 1000.0 | 1000.0 | 1000.0 | 1000.0 | 1000.0 |

Example 2

Tables 3 to 7 which follow mention use-specific properties of the abovementioned microemulsions 2, 6 and 10.

TABLE 3

| ME serial number | | 2 | 6 | 10 |
|---|---|---|---|---|
| Visual assessment | beginning | clear | clear | clear |
| | after 2 weeks' storage at 54° C. | clear | clear | clear |
| | after 6 weeks' storage at −10° C. | clear | clear | clear |
| | after 6 weeks' storage at 50° C. | clear | clear | clear |
| | after 8 weeks' storage at 40° C. | clear | clear | clear |
| | after 12 weeks' storage at 35° C. | clear | clear | clear |
| Active ingredient concentration in the microemulsion, absolute [g/l] | beginning | 47.25 | 48.98 | 50.22 |
| | after 2 weeks' storage at 54° C. | 46.63 | 49.00 | 50.45 |
| | after 6 weeks' storage at −10° C. | 46.68 | 48.81 | 50.25 |
| | after 6 weeks' storage at 50° C. | 46.48 | 48.95 | 50.25 |
| | after 8 weeks' storage at 40° C. | 46.78 | 48.95 | 50.55 |
| | after 12 weeks' storage at 35° C. | 46.78 | 48.51 | 50.45 |
| Active ingredient concentration in the microemulsion, relative [%] | beginning | 100.00 | 100.00 | 100.00 |
| | after 2 weeks' storage at 54° C. | 98.69 | 100.04 | 100.46 |
| | after 6 weeks' storage at −10° C. | 98.79 | 99.65 | 100.06 |
| | after 6 weeks' storage at 50° C. | 98.37 | 99.94 | 100.06 |
| | after 8 weeks' storage at 40° C. | 99.01 | 99.94 | 100.66 |
| | after 12 weeks' storage at 35° C. | 99.01 | 99.04 | 100.46 |

TABLE 4

| ME serial number | | 2 | 6 | 10 |
|---|---|---|---|---|
| pH (undiluted) | beginning | 7.0 | 5.6 | 6.1 |
| | after 2 weeks' storage at 54° C. | 6.8 | 5.1 | 5.8 |
| | after 6 weeks' storage at −10° C. | 7.0 | 5.7 | 6.2 |
| | after 6 weeks' storage at 50° C. | 6.7 | 4.9 | 5.5 |
| | after 8 weeks' storage at 40° C. | 6.9 | 5.0 | 5.8 |
| | after 12 weeks' storage at 35° C. | 6.9 | 5.0 | 5.8 |
| pH (50% diluted) | beginning | 6.2 | 4.4 | 4.5 |
| | after 2 weeks' storage at 54° C. | 5.0 | 3.9 | 4.2 |
| | after 6 weeks' storage at −10° C. | 6.4 | 4.6 | 4.7 |
| | after 6 weeks' storage at 50° C. | 5.6 | 3.7 | 4.0 |
| | after 8 weeks' storage at 40° C. | 5.9 | 3.8 | 4.2 |
| | after 12 weeks' storage at 35° C. | 5.9 | 3.9 | 4.3 |
| pH (1% diluted) | beginning | 5.2 | 4.6 | 4.4 |
| | after 2 weeks' storage at 54° C. | 5.1 | 4.0 | 4.2 |
| | after 6 weeks' storage at −10° C. | 5.3 | 4.6 | 4.5 |
| | after 6 weeks' storage at 50° C. | 5.0 | 4.0 | 4.0 |
| | after 8 weeks' storage at 40° C. | 5.1 | 4.2 | 4.2 |
| | after 12 weeks' storage at 35° C. | 5.1 | 4.2 | 4.2 |

TABLE 5

| ME serial number | | 2 | 6 | 10 |
|---|---|---|---|---|
| Surface tension (undiluted) [mN/m] | beginning | 30.8 | 31.0 | 32.1 |
| | after 2 weeks' storage at 54° C. | 28.9 | 31.0 | 31.6 |
| | after 6 weeks' storage at −10° C. | 30.6 | 31.1 | 32.1 |
| | after 6 weeks' storage at 50° C. | 30.5 | 31.0 | 31.6 |
| | after 8 weeks' storage at 40° C. | 30.4 | 30.8 | 32.0 |
| | after 12 weeks' storage at 35° C. | 30.6 | 31.0 | 32.2 |
| Surface tension (50% diluted) [mN/m] | beginning | 28.4 | 28.5 | 23.6 |
| | after 2 weeks' storage at 54° C. | 27.5 | 28.4 | 28.6 |
| | after 6 weeks' storage at −10° C. | 25.9 | 28.1 | 28.9 |
| | after 6 weeks' storage at 50° C. | 28.5 | 28.4 | 28.1 |
| | after 8 weeks' storage at 40° C. | 28.4 | 28.0 | 29.1 |
| | after 12 weeks' storage at 35° C. | 24.2 | 28.1 | 28.7 |
| Viscosity (undiluted) at D = 100 1/s [mPas] | beginning | 30 | 33 | 26 |
| | after 2 weeks' storage at 54° C. | 31 | 32 | 27 |
| | after 6 weeks' storage at −10° C. | 31 | 33 | 27 |
| | after 6 weeks' storage at 50° C. | 32 | 33 | 28 |
| | after 8 weeks' storage at 40° C. | 31 | 30 | 27 |
| | after 12 weeks' storage at 35° C. | 26 | 31 | 27 |

Double-distilled water is used for the dilution.

TABLE 6

| ME serial number | | 2 | 6 | 10 |
|---|---|---|---|---|
| Ross-Miles foam test (50% diluted) in CIPAC D water | beginning | 90 mm | 90 mm | 130 mm |
| | after 1 minute | 90 mm | 70 mm | 120 mm |
| | after 3 minutes | 80 mm | 70 mm | 120 mm |
| | after 5 minutes | 60 mm | 50 mm | 50 mm |
| | after 15 minutes | 10 mm | 10 mm | 10 mm |

Example 3

Experiments with the microemulsions 11 to 16 according to the invention are carried out in order to determine the plant-protectant effect. To this end, the microemulsions 11 to 16 are applied, at concentrations of 25, 50, 75 and 100 ppm, to diseased wheat plants by drenching. Experiments 1 to 12, in which a prior-art standard preparation comprising Neodol, a $C_9$-$C_{11}$-alcohol ethoxylated with 6 ethylene oxide units (standard, experiments 1 to 4), an emulsion (experiments 5 to 8) and a suspension (experiments 9 to 12) are used, serve as comparative experiments. The active ingredient in all experiments is metconazole. To evaluate the experiments, those plants which are still diseased after the treatment are counted.

The results of the experiments are shown in Table 7.

TABLE 7

| | | | Number of plants which are still diseased [%] | | | |
|---|---|---|---|---|---|---|
| Exp. No. | Sample/ME | Concentration in ppm | Pot 1 | Pot 2 | Pot 3 | Ø |
| 1 | Standard | 100 | 0 | 0 | 0 | 0 |
| 2 | | 75 | 0 | 0 | 0 | 0 |
| 3 | | 50 | 7 | 3 | 3 | 4 |
| 4 | | 25 | 60 | 40 | 50 | 50 |
| 5 | Emulsion | 100 | 7 | 7 | 10 | 8 |
| 6 | | 75 | 50 | 40 | 50 | 47 |
| 7 | | 50 | 80 | 80 | 80 | 80 |
| 8 | | 25 | 90 | 90 | 90 | 90 |
| 9 | Suspension | 100 | 70 | 60 | 80 | 70 |
| 10 | | 75 | 70 | 70 | 80 | 73 |
| 11 | | 50 | 80 | 80 | 80 | 80 |
| 12 | | 25 | 90 | 90 | 90 | 90 |
| 13 | 11 | 100 | 0 | 0 | 0 | 0 |
| 14 | | 75 | 0 | 0 | 0 | 0 |
| 15 | | 50 | 7 | 7 | 7 | 7 |
| 16 | | 25 | 70 | 60 | 60 | 63 |
| 17 | 12 | 100 | 0 | 0 | 0 | 0 |
| 18 | | 75 | 1 | 3 | 0 | 1 |
| 19 | | 50 | 5 | 5 | 7 | 6 |
| 20 | | 25 | 30 | 30 | 50 | 37 |
| 21 | 13 | 100 | 0 | 0 | 0 | 0 |
| 22 | | 75 | 0 | 1 | 3 | 1 |
| 23 | | 50 | 3 | 5 | 5 | 4 |
| 24 | | 25 | 70 | 60 | 60 | 63 |
| 25 | 14 | 100 | 0 | 0 | 0 | 0 |
| 26 | | 75 | 1 | 0 | 1 | 1 |
| 27 | | 50 | 5 | 5 | 5 | 5 |
| 28 | | 25 | 60 | 60 | 50 | 57 |
| 29 | 15 | 100 | 0 | 0 | 0 | 0 |
| 30 | | 75 | 0 | 0 | 1 | 0 |
| 31 | | 50 | 5 | 10 | 10 | 8 |
| 32 | | 25 | 50 | 60 | 50 | 53 |
| 33 | 16 | 100 | 0 | 0 | 0 | 0 |
| 34 | | 75 | 0 | 1 | 3 | 1 |
| 35 | | 50 | 3 | 5 | 7 | 5 |
| 36 | | 25 | 60 | 50 | 60 | 57 |

We claim:

1. A micro emulsion comprising:
   (a) 0.1 to 50% by weight of at least one active ingredient selected from the group consisting of fungicides, insecticides, nematicides, herbicides, growth regulators and combinations thereof as component A;
   (b) 0.5 to 40% by weight of at least one solvent which is fully miscible with water wherein said solvent is selected from the group consisting of 1-methoxy-2-propanol acetate, methyl-proxitol-acetate, propylene-glycol-mono-methyl ether acetate, n-propyl lactate, esters of benzoic acid, esters of dicarboxylic acids, cyclic esters, cyclic amides, carbonates, and mixtures thereof, as component B; or
   0.5 to 40% by weight of sulphur containing solvents in mixture with at least one additional solvent selected from the group consisting of 1-methoxy-2-propanol acetate, methyl-proxitol-acetate, propylene-glycol-mono-methyl ether acetate, n-propyl lactate, esters of benzoic acid, of dicarboxylic acids, cyclic esters, cyclic amides, and carbonates as component B;
   (c) 10 to 40% by weight of at least one nonionic surfactant as component C;
   (d) 0 to 10% by weight of further additives as component D;
   (e) 10 to 90% by weight of water as component E;
   and
   (f) 0.1 to 60% by weight of at least one di-$C_1$-$C_4$-alkylamide of fatty acids comprising 6 to 16 carbon atoms as component F,
   wherein each case is based on the total microemulsion, where the total of the amounts of components A, B, C, D, E and F is 100% by weight and where the microemulsion has an anionic surfactant content of ≤1% by weight, based on the total amount of the micro emulsion.

2. The micro emulsion of claim 1, wherein the at least one nonionic surfactant present in the micro emulsion is selected from the group consisting of compounds which are formed by alkoxylating compounds with at least one active hydrogen atom, alkoxylates of alkylphenols, block polymers of $C_2$-$C_6$-alkylene oxides, alkylglycosides and combinations thereof.

3. The micro emulsion of claim 1, consisting of the components A, B, C, E and F.

4. A process for the preparation of the micro emulsion of claim 1, comprising mixing components A, B, C, optionally D, E and F.

5. The process of claim 4, wherein said mixing is carried out at room temperature.

6. A method of controlling pests comprising contacting the pests or their food supply, habitat, breeding grounds or their locus with a pesticidally effective amount of the micro emulsion of claim 1 wherein a plant, a tree, soil or a seed is protected.

7. The method of claim 6, wherein said pests are insects, nematodes, or fungi.

8. The method of claim 6, wherein the microemulsion is present as a dilute aqueous solution.

9. A method of controlling weeds comprising contacting said weeds or their locus with a herbicidally effective amount of the microemulsion of claim 1.

10. The method of claim 9, wherein the microemulsion is present as a dilute aqueous solution.

11. The microemulsion of claim 1, wherein component B is 0.5 to 40% by weight of sulphur containing solvents in mixture with at least one additional solvent selected from the group consisting of 1-methoxy-2-propanol acetate, methylproxitol-acetate, propylene-glycol-mono-methyl ether acetate, gamma-butyrolactone, and n-propyl lactate.

12. A micro emulsion comprising:
- (a) 0.1 to 50% by weight of at least one active ingredient selected from the group consisting of fungicides, insecticides, nematicides, herbicides, growth regulators and combinations thereof as component A;
- (b) 0.5 to 40% by weight of at least one solvent which is fully miscible with water wherein said solvent is selected from the group consisting of sulphur containing solvents as component B;
- (c) 10 to 40% by weight of at least one nonionic surfactant as component C;
- (d) 0 to 10% by weight of further additives as component D;
- (e) 10 to 90% by weight of water as component E; and
- (f) 0.1 to 60% by weight of at least one solvent, which is partially miscible with water selected from the group consisting of di-$C_1$-$C_4$-alkylamide of fatty acids comprising 6 to 16 carbon atoms and at least one additional solvent selected from the group consisting of 2-heptanone, 3-heptanone, 4-heptanone, acetophenone, cyclohexanone, and tri-$C_1$-$C_6$ alkyl phosphates and mixtures thereof as component F;

and
wherein each case is based on the total microemulsion, where the total of the amounts of components A, B, C, D, E and F is 100% by weight and where the microemulsion has an anionic surfactant content of ≤1% by weight, based on the total amount of the micro emulsion.

13. The micro emulsion of claim 12, wherein the at least one nonionic surfactant present in the micro emulsion is selected from the group consisting of compounds which are formed by alkoxylating compounds with at least one active hydrogen atom, alkoxylates of alkylphenols, block polymers of $C_2$-$C_6$-alkylerie oxides, alkylglycosides and combinations thereof.

14. The micro emulsion of claim 13, consisting of the components A, B, C, E and F.

15. The micro emulsion of claim 1, wherein component D is selected from the group consisting of: humectants, dispersants, non-anionic surface-active substances, inorganic salts, oligo- or polyphosphates, carbonates, fertilizers, phosphorus- and potassium-compounds, trace elements, antifoams, binders, polyamino acids, polyvinyl alcohols, polyvinylpyrrolidone, polyacrylic acid derivatives, polymers, colorants, stabilizers, biocides, vegetable oils, high-boiling hydrocarbons, and preservatives.

* * * * *